(12) United States Patent
Joye et al.

(10) Patent No.: US 6,972,015 B2
(45) Date of Patent: Dec. 6, 2005

(54) CRYOSURGICAL FLUID SUPPLY

(75) Inventors: James Joye, Monte Sereno, CA (US); Richard S. Williams, Redwood City, CA (US); Ronald Williams, Menlo Park, CA (US)

(73) Assignee: CryoVascular Systems, Inc., Los Gatos, CA (US)

( * ) Notice: Subject to any disclaimer, the term of this patent is extended or adjusted under 35 U.S.C. 154(b) by 82 days.

(21) Appl. No.: 10/785,503

(22) Filed: Feb. 23, 2004

(65) Prior Publication Data

US 2004/0167505 A1   Aug. 26, 2004

Related U.S. Application Data

(63) Continuation of application No. 10/105,577, filed on Mar. 21, 2002, now Pat. No. 6,786,901, which is a continuation of application No. 09/268,205, filed on Mar. 15, 1999, now Pat. No. 6,432,102.

(51) Int. Cl.⁷ .............................................. A61B 18/18
(52) U.S. Cl. ...................... 606/21; 606/22; 251/129.22
(58) Field of Search ........................ 606/21–23, 25–26; 251/129.01, 129.08, 129.15, 129.22

(56) References Cited

U.S. PATENT DOCUMENTS

| | | | |
|---|---|---|---|
| 3,125,096 A | 3/1964 | Antiles et al. | |
| 3,630,203 A | 12/1971 | Sellinger et al. | |
| 3,901,241 A | 8/1975 | Allen, Jr. | |
| 4,336,691 A | 6/1982 | Burstein et al. | |
| 4,754,752 A | 7/1988 | Ginsburg et al. | |
| 4,946,460 A | 8/1990 | Merry et al. | |
| 5,019,075 A | 5/1991 | Spears et al. | |
| 5,041,089 A | 8/1991 | Mueller et al. | |
| 5,078,713 A | 1/1992 | Varney | |
| 5,092,841 A | 3/1992 | Spears | |
| 5,106,360 A | 4/1992 | Ishiwara et al. | |
| 5,109,859 A * | 5/1992 | Jenkins ........................ 600/439 |
| 5,117,870 A | 6/1992 | Goodale et al. | |
| 5,147,355 A | 9/1992 | Friedman et al. | |
| 5,151,100 A | 9/1992 | Abele et al. | |

(Continued)

FOREIGN PATENT DOCUMENTS

WO    WO 91/05528 A1    5/1991

(Continued)

OTHER PUBLICATIONS

CMS Website Information "Cryomedical Science Introduces Cryolite®", Downloaded from Internet <<http://www.cryo-medical.com/R&D/cryolite.htm>> (Nov. 22, 1998) 3 pages total.

(Continued)

*Primary Examiner*—Roy D. Gibson
(74) *Attorney, Agent, or Firm*—Townsend & Townsend & Crew LLP; Mark D. Barrish

(57) ABSTRACT

Improved systems, devices, and methods for delivering cryogenic cooling fluid to cryosurgical probes such as cryosurgical endovascular balloon catheters take advantage of the transients during the initiation and termination of cryogenic fluid flow to moderate the treatment temperatures of tissues engaged by the probe. A flow limiting element along a cryogenic fluid path intermittently interrupts the flow of cooling fluid, often cycling both the fluid flow and treatment temperature. This can maintain the tissue treatment temperature within a predetermined range which is above the treatment temperature provided by a steady flow of cryogenic fluid. In another aspect, room temperature single-use cooling fluid cartridges are filled with a sufficient quantity of cryosurgical fluid to effect a desired endovascular cryosurgical treatment.

7 Claims, 4 Drawing Sheets

U.S. PATENT DOCUMENTS

| | | | |
|---|---|---|---|
| 5,190,539 A | 3/1993 | Fletcher et al. |
| 5,191,883 A | 3/1993 | Lennox et al. |
| 5,196,024 A | 3/1993 | Barath |
| 5,275,595 A | 1/1994 | Dobak, III |
| 5,342,301 A | 8/1994 | Saab |
| 5,458,612 A | 10/1995 | Chin |
| 5,486,208 A | 1/1996 | Ginsburg |
| 5,501,681 A | 3/1996 | Neuwirth et al. |
| 5,545,195 A | 8/1996 | Lennox et al. |
| 5,617,739 A | 4/1997 | Little |
| 5,644,502 A | 7/1997 | Little |
| 5,667,521 A | 9/1997 | Keown |
| 5,733,280 A | 3/1998 | Avitall |
| 5,814,040 A | 9/1998 | Nelson et al. |
| 5,820,626 A | 10/1998 | Baumgardner |
| 5,846,235 A | 12/1998 | Pasricha et al. |
| 5,868,735 A | 2/1999 | Lafontaine |
| 5,899,898 A | 5/1999 | Arless et al. |
| 5,899,899 A | 5/1999 | Arless et al. |
| 5,902,299 A | 5/1999 | Jayaraman et al. |
| 5,971,979 A | 10/1999 | Joye et al. |
| 6,027,499 A | 2/2000 | Johnston et al. |
| 6,241,718 B1 | 6/2001 | Arless et al. |
| 6,290,696 B1 | 9/2001 | Lafontaine |
| 6,355,029 B1 | 3/2002 | Joyce et al. |
| 6,368,304 B1 * | 4/2002 | Aliberto et al. ............. 604/113 |
| 6,379,378 B1 | 4/2002 | Werneth et al. |
| 6,432,102 B2 | 8/2002 | Joyce et al. |
| 6,517,533 B1 | 2/2003 | Swaminathan |
| 6,575,933 B1 | 6/2003 | Wittenberger et al. |
| 6,652,565 B1 | 11/2003 | Shimada et al. |

FOREIGN PATENT DOCUMENTS

| | | |
|---|---|---|
| WO | WO 98/37822 A1 | 9/1998 |
| WO | WO 98/38934 A1 | 9/1998 |
| WO | WO 98/52479 A1 | 9/1998 |
| WO | WO 99/35986 A1 | 7/1999 |
| WO | WO 00/42931 A1 | 7/2000 |
| WO | WO 01/64145 A1 | 9/2001 |
| WO | WO 02/38091 A1 | 5/2002 |

OTHER PUBLICATIONS

CMS Website Information "Cell Suicide Following Cryosurgery", Downloaded from Internet <<http://www.cryomedical.com/R&D/apoptosi.htm>> (Mar. 8, 1999) 3 pages total.

Meinhard Nebulizer, "The Meinhard® Concentric Glass Nebulizer," Downloaded from Internet << http://web.archive.org/web/19990221174248/www.meinhard.com/product3.htm.>> (Aug. 10, 2004) 6 pages total.

U.S. Appl. No. 09/344,177, filed on Jun. 24, 1999 entitled: *Cryosurgical Catheter Inhibition of Hyperplasia*, Inventor(s): James Joye et al.

U.S. Appl. No. 60/121,638, filed on Feb. 24, 1999 entitled: *Cryogenic Angioplasty Catheter*, Inventor(s): James Joye et al.

U.S. Appl. No. 60/121,637, filed on Feb. 24, 1999 entitled: *Cryogenic Angioplasty Catheter*, Inventor(s): James Joye et al.

\* cited by examiner

CRYOSURGICAL FLUID SUPPLY

CROSS-REFERENCES TO RELATED APPLICATIONS

The present application is a continuation patent application of U.S. U.S. patent application Ser. No. 10/105,577 filed Mar. 21, 2002, now U.S. Pat. No. 6,786,901, which is a continuation U.S. patent application Ser. No. 09/268,205 filed Mar. 15, 1999, now U.S. Pat. No. 6,432,102, the full disclosures of which are incorporated herein by reference.

BACKGROUND OF THE INVENTION

1. Field of the Invention

The present invention relates generally to apparatus and methods for cryosurgical therapy. In a particular embodiment, the invention provides a cryosurgical fluid delivery system which makes use of transients in the cooling cycle to moderate the cooling effects of a cryosurgical endovascular balloon catheter.

A number of percutaneous intravascular procedures have been developed for treating atherosclerotic disease in a patient's vasculature. The most successful of these treatments is percutaneous transluminal angioplasty (PTA). PTA employs a catheter having an expansible distal end (usually in the form of an inflatable balloon) to dilate a stenotic region in the vasculature to restore adequate blood flow beyond the stenosis. Other procedures for opening stenotic regions include directional atherectomy, rotational atherectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the subsequent occurrence of restenosis.

Restenosis refers to the re-narrowing of an artery following an initially successful angioplasty or other primary treatment. Restenosis typically occurs within weeks or months of the primary procedure, and may affect up to 50% of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While these proposals have enjoyed varying levels of success, no one of these procedures is proven to be entirely successful in avoiding all occurrences of restenosis and hyperplasia.

It has recently been proposed to prevent or slow reclosure of a lesion following angioplasty by remodeling the lesion using a combination of dilation and cryogenic cooling. Co-pending U.S. patent application Ser. No. 09/203,011 filed Dec. 1, 1998, the full disclosure of which is incorporated herein by reference, describes an exemplary structure and method for inhibiting restenosis using a cryogenically cooled balloon. While these proposals appear promising, the described structures and methods for carrying out endovascular cryogenic cooling would benefit from still further improvements. For example, the mechanical strength of the vasculature generally requires quite a high pressure to dilate the vessel during conventional angioplasty. Conventional angioplasty often involves the inflation of an angioplasty balloon with a pressure of roughly 10 bar. These relatively high pressures can be safely used within the body when balloons are inflated with a benign liquid such as contrast or saline. However, high pressures involve some risk of significant injury should the balloon fail to contain a cryogenic gas or liquid/gas combination at these high pressures. Additionally, work in connection with the present invention has shown that the antiproliferative efficacy of endoluminal cryogenic systems can be quite sensitive to the temperature to which the tissues are cooled: although commercially available, cryogenic cooling fluids show great promise for endovascular use, it can be challenging to reproducibly effect controlled cooling without having to resort to complex, high pressure, tight tolerance, and/or expensive cryogenic control components.

For these reasons, it would be desirable to provide improved devices, systems and methods for effecting cryosurgical and/or other low temperature therapies. It would further be desirable if these improved techniques were capable of delivering cryosurgical cooling fluids into the recently proposed endovascular cryosurgical balloon catheters, as well as other known cryosurgical probes. It would be particularly desirable if these improved techniques delivered the cryosurgical cooling fluid in a safe and controlled manner so as to avoid injury to adjacent tissues, ideally without requiring a complex control system and/or relying entirely on the operator's skill to monitor and control these temperature-sensitive treatments.

2. Description of the Background Art

A cryoplasty device and method are described in WO 98/38934. Balloon catheters for intravascular cooling or heating of a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691. The following U.S. Patents may also be relevant to the present invention: U.S. Pat. Nos. 5,458,612; 5,545,195; and 5,733,280.

The full disclosures of each of the above U.S. patents are incorporated by reference.

SUMMARY OF THE INVENTION

The present invention generally overcomes the advantages of the prior art by providing improved systems, devices, and methods for delivering cryogenic cooling fluid to cryosurgical probes, such as the new cryosurgical endovascular balloon catheters. The invention generally takes advantage of the transients during the initiation and termination of cryogenic fluid flow to moderate the treatment temperatures of tissues engaged by the probe. In some embodiments, a flow limiting element along a cryogenic fluid path intermittently interrupts the flow of cooling fluid, often cycling both the fluid flow and treatment temperature. This can help maintain the tissue treatment temperature within a predetermined range which is significantly above the treatment temperature which would be provided by a steady flow of cryogenic fluid. This intermittent flow may decrease sensitivity of the system to the particular configuration of the exhaust gas of flow path defined by a flexible catheter body disposed within the vascular system. Cooling of the vessel along the catheter body proximally of a balloon may also be decreased, thereby avoiding the embolization of frozen blood within the vasculature. In another aspect, the invention makes use of a single-use cooling fluid cartridges which may be transported safely at room temperature when filled with a sufficient quantity of cryosurgical fluid to effect a desired treatment, and which can be safely and cost-effectively disposed of after use.

In a first aspect, the invention provides a cryogenic fluid delivery system for use with a cryogenic probe having a cryogenic fluid input and a cooling surface for engaging a target tissue. The cryogenic delivery system comprises a cooling fluid container having a cryogenic fluid output. A cooling fluid path couples the fluid output of the container to the fluid input of the probe. A flow interrupter disposed along the cooling fluid path intermittently inhibits the flow of cryogenic cooling fluid from the container to the probe so as to limit cooling by the cooling surface.

A variety of flow interrupter structures may be used to moderate cooling of the target tissue. For example, the flow interrupter may comprise a solenoid valve, which will often be driven by a simple intermittent timing switch, a timing circuit, or the like. Alternatively, the flow interrupter may comprise a valve member rotatably engaging a valve body so as to provide fluid communication when the valve member is in a first rotational position and inhibit fluid communication when the valve is in a second rotational position. Such a rotatable valve assembly will often be driven by a motor, such as an electric motor, a pneumatic motor, or the like. Still further alternative fluid interrupters may comprise a deformable cryogenic conduit which can be occluded by actuation of a solenoid, pneumatic ram, or the like.

In another aspect, the invention provides a cryogenic fluid delivery system for use with a cryogenic probe. The probe has a cryogenic fluid input and a cooling surface, and the delivery system includes a cooling fluid container having a cryogenic fluid output. A cryogenic cooling fluid is disposed in the fluid container, and a cooling fluid path couples the fluid output of the container to the fluid input of the probe. Means are disposed along the cooling fluid path for limiting cooling of the cooled surface by intermittently inhibiting cooling fluid flow from the container to the probe.

In another aspect, the invention provides a single-use cryogenic fluid delivery system for use with a cryogenic endovascular catheter so as to inhibit hyperplasia of a diseased blood vessel region of a patient body. The cryogenic delivery system comprises a cooling fluid container and a connector for coupling to the catheter. A cooling fluid path provides fluid communication from the container to the connector. The path has a seal, and a cryogenic cooling fluid is disposed within the fluid container. The cooling fluid has a quantity and is at a pressure such that the catheter will cool the blood vessel to a temperature in a predetermined temperature range so as to inhibit hyperplasia when the connector is coupled to the catheter and the seal is opened.

Advantageously, the cryogenic fluid may be stored and transported at the desired pressure by the container when the container is at room temperature. The quantity of cryogenic fluid may be sufficient to maintain the blood vessel within the treatment temperature range for a time in predetermined treatment time range, thereby allowing the cooling system to be substantially self-controlling. Such a system is particularly useful for inhibiting hyperplasia or neoplasia, the quantity and pressure of the cryogenic fluid ideally being sufficient to cool a surface of the diseased blood vessel region to a temperature from about −5° C. to about −25° C. for a time from about 10 to about 60 seconds, most often for a time between about 20 and 30 seconds.

The container will often comprise a disposable cartridge having a frangible seal. The seal may be breached by a fitting which threadably engages a casing in which the container is received. Such disposable cartridges can safely maintain cryosurgical cooling fluids such as $N_2O$ at high pressures and in sufficient quantities to effect a variety of desired treatments. For example, the cartridge may contain about 5 to 30 grams of cooling fluid, and may contain $N_2O$ or other cooling fluids at a pressure between about 400 and 1000 psi.

In a method aspect of the present invention, a tissue of a patient body can be treated using a cooling surface of a cryosurgical probe. Such a method may comprise coupling a cryogenic fluid canister to the probe, the canister containing a pressurized cryogenic cooling fluid. The cooling fluid flows from the canister toward the cooling surface of the probe. The flow is intermittently interrupted to limit cooling of the tissue by the probe.

The interruption periodically inhibits the flow of cooling fluid to avoid cooling of a tissue below a predetermined temperature range. This can repeatedly cycle a tissue temperature, ideally reaching a temperature within a range from about −5° C. to about −25° C. for a time in a range from about 10 to about 60 seconds during the cycle, most often for a time between about 20 and 30 seconds. Typically, the cycling of the flow interruption and/or tissue temperature will have a period in a range from about 0.01 second to about 5 seconds, the frequency ideally being in a range from about 0.3 to about 3 hertz.

While this summary describes many of the optional, preferred features of the exemplary embodiments, it should be understood that the invention is not limited to these specific embodiments. A fuller understanding of the specific embodiments and their operation can be obtained with reference to the drawings and description which follow.0

DESCRIPTION OF THE SPECIFIC EMBODIMENTS

The devices, systems, and methods of the present invention are related to co-pending U.S. patent application Ser. No. 09/203,011, filed on Dec. 1, 1998 for an Apparatus and Method for Cryogenic Inhibition of Hyperplasia, and to co-pending U.S. patent application Ser. No. 60/121,638, filed Feb. 24, 1999 for a Cryogenic Angioplasty Catheter. These applications are assigned to the present assignee, and their full disclosures are incorporated herein by reference.

Figure 1:
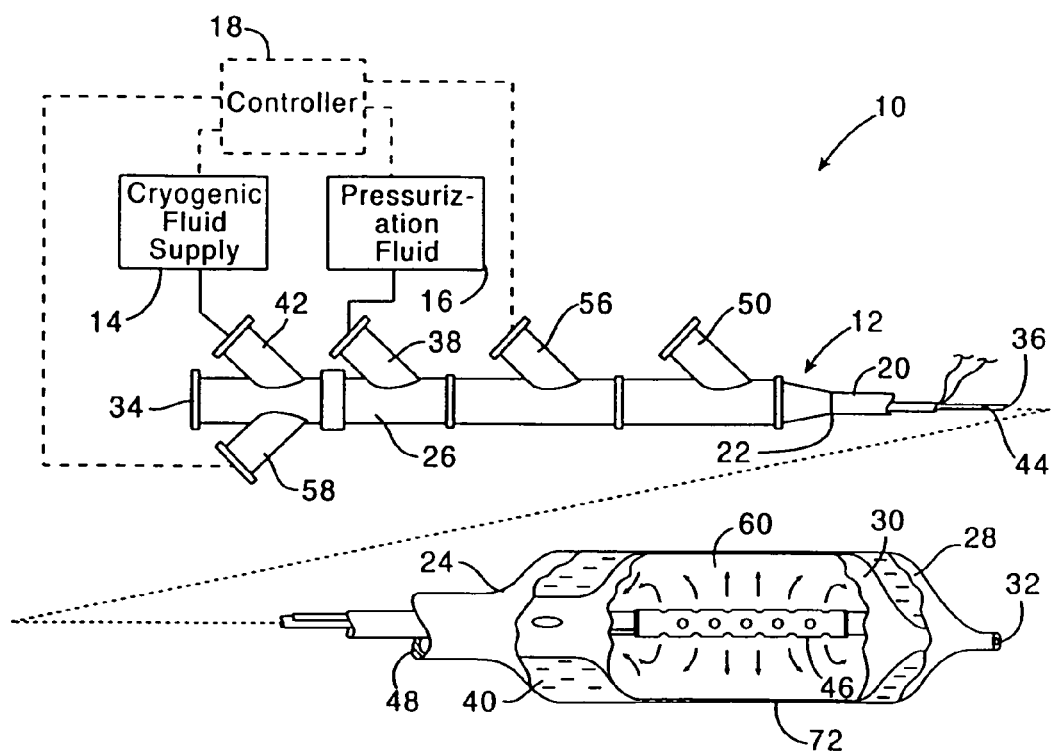
FIG. 1 schematically illustrates a cryogenic/angioplasty balloon catheter system including a cryogenic fluid supply system according to the principles of the present invention.

Referring now to FIG. 1, an exemplary system 10 is capable of treating a diseased vessel wall of a blood vessel using a combination of both angioplasty dilation and cryogenic cooling. In general, system 10 includes a catheter 12 coupled to a cryogenic fluid supply system 14 and an angioplasty pressurization system 16. One or both of cryogenic system 14 and pressurization system 16 may optionally be operatively coupled to a controller 18 for coordination of cooling and dilation. In some embodiments, controller 18 may actively control cryogenic cooling by modulating cooling fluid supply rates, cooling exhaust gas port pressures, cycling of the cooling fluid flow, or the like, in response to balloon pressure, measured temperature, or the like. In other embodiments, the system will be substantially self-modulating through the use of predetermined supply quantities, pressures, and/or flow cycling rates.

Catheter 12 generally includes a catheter body having a proximal end 22 and a distal end 24. A proximal housing 26 includes a number of ports for coupling of cryogenic supply system 14, pressurization system 16, and the like, to the proximal end of the catheter body. An angioplasty balloon 28 and a cryogenic balloon 30 are mounted near the distal end of catheter body 24. A catheter body will generally be flexible and contain a plurality of lumens to provide fluid communication between the ports of proximal housing 26 and balloons 28 and 30.

Angioplasty balloon 28 may be formed from a variety of materials conventionally used for dilating blood vessels. Angioplasty balloon 28 will typically comprise a non-distensible material such as polyethylene terephthalate (PET). Such angioplasty balloons are formed in a variety of sizes depending on their intended use, typically having a length and range from about 15 mm to about 50 mm and an expanded diameter in a range from about 2 mm to about 10 mm. Prior to inflation, angioplasty balloon 28 will generally remain in a low profile configuration suitable for insertion into and maneuvering through the vascular system. A guidewire lumen 32 extends through angioplasty balloon 28 and cryogenic balloon 30 from a proximal guidewire port 34 to facilitate accessing the target treatment site.

High contrast markers may be provided within balloon 30 to enhance an image of the distal end of the catheter and facilitate positioning of the balloon fluoroscopically, sonographically, or under any other alternative image modality (with appropriate contrast structures). Such markers may be formed by winding a gold or platinum wire around the tubular structure defining a pressurization lumen 36. Angioplasty balloon 28 is inflated by injecting contrast fluid 40 from pressurization system 16 into pressurization lumen 36 through a pressurization port 38. In this embodiment, balloon 28 is isolated from balloon 30, so as to avoid inadvertent inflation of the cryogenic balloon during dilation.

In the catheter illustrated in FIG. 1, cryogenic balloon 30 is nested within the angioplasty balloon 28. It should be understood that cryogenic balloon 30 may alternatively be axially displaced from the cryogenic balloon, or that a single balloon may function as both the cryogenic cooling and dilation. Cooling may be provided by containing the cryogenic cooling fluid within a rigid heat exchanger, and optionally cooling a surrounding balloon wall via a fluid having a predetermined freezing temperature. In still further alternative embodiments, cryogenic cooling catheters may be provided without dilation capabilities. Still further alternative cooling probes might benefit from the modulated cooling of the present invention, including hand-held probes connected to cooling surfaces by rigid shafts. In other words, many probe structures might benefit from the present invention. It should be understood that the supply system need not be separate or separable from the probe.

Regardless of the specific structure of the cooling surface, cryogenic fluid 60 is generally directed from an output of cryogenic fluid supply 14 to an input of the cooling probe. In the embodiment of FIG. 1, the cryogenic fluid is injected into a cryogenic supply port 42 and passes toward cryogenic balloon 30 through cryogenic supply lumen 44 within catheter body 20. Cryogenic fluid 60 may comprise cryogenic liquids or liquid/gas mixtures, optionally including carbon dioxide ($CO_2$), nitrous oxide ($N_2O$), liquid nitrogen ($N_2$), a fluorocarbon such as AZ-50™ (sold by Genetron of Morristown, N.J.), or the like. As cryogenic liquid 60 passes from the supply lumen and into cryogenic balloon 30, it may be distributed both radially and axially by a diffuser 46. Diffuser 46 will generally comprise a tubular structure with radially oriented openings. As the openings are radially oriented, diffuser 46 will direct the cooling fluid roughly perpendicularly toward the wall of cryogenic balloon 30, so that the heat transfer coefficient between the cooling vapor and balloon wall is quite even and quite high. This helps to reduce the temperature of the balloon wall, and provides greater heat extraction for a given flow rate of coolant. Additionally, as the ports are distributed both circumferentially and axially along the balloon, the diffuser can provide a substantially uniform cooling over a significant portion of (often over the majority of) the surface of the balloon.

In some embodiments, the cryogenic cooling fluid may pass through a Joule-Thompson orifice between fluid supply lumen 44 and balloon 30. In other embodiments, at least a portion of the cryogenic cooling fluid may exit one or more ports into the balloon as a liquid. The liquid will vaporize within the balloon, and the enthalpy of vaporization can help cool the surrounding vessel wall. The liquid may coat at least a portion of the balloon wall so as to enhance even cooling over at least a portion of the vessel wall. Hence, the ports of diffuser 46 may have a total cross-section which is smaller than a cross-section of the fluid supply lumen 44, or which is at least as large as (or larger than) the cross-section of the fluid supply lumen.

After the cryogenic cooling fluid vaporizes within balloon 30, it escapes the balloon proximally along an exhaust lumen 48, and is exhausted from catheter 12 through an exhaust port 50. Inflation of cryogenic balloon 30 may be controlled by the amount of cryogenic fluid injected into the balloon, and/or by the pressure head loss experienced by the exhaust gases. Cooling is generally enhanced by minimizing the pressure within balloon 30. To take advantage of this effect so as to control the amount of cooling, a fixed or variable orifice may be provided at exhaust port 50. Alternatively, a vacuum might be applied to the exhaust port to control cooling and enhance cooling efficiency. In some embodiments, a layer of insulting material 72 may be disposed between the cryogenic cooling fluid and the tissue engaging surface of the balloon. A suitable insulation material might include a thin layer of expanded Teflon™ (ePTFE) on an inner or outer surface of cryogenic balloon 30, on an inner or outer surface of angioplasty balloon 28, or the like. A wide variety of alternative insulation materials might also be used.

To accurately control and/or monitor the pressure within cryogenic balloon 30, proximal housing 26 may include a cooling balloon pressure monitoring port 56. The pressure monitoring port will be in fluid communication with the cryogenic balloon 30, preferably through a dedicated pressure monitoring lumen (not shown). Signals from pressure monitoring port 56 and a thermocouple connector 58 may be transmitted to the controller 18.

In use, the nested cryogenic/angioplasty balloon catheter of FIG. 1 may allow pre-cooling of a diseased vessel wall prior to dilation, cooling of a vessel wall after dilation, interspersed cooling/dilation, and even concurrent dilation during cooling. In some endovascular therapies, cooling without dilation may be desired, so that no provisions for inflation of an angioplasty balloon 28 by contrast 40 are required.

Figure 2:
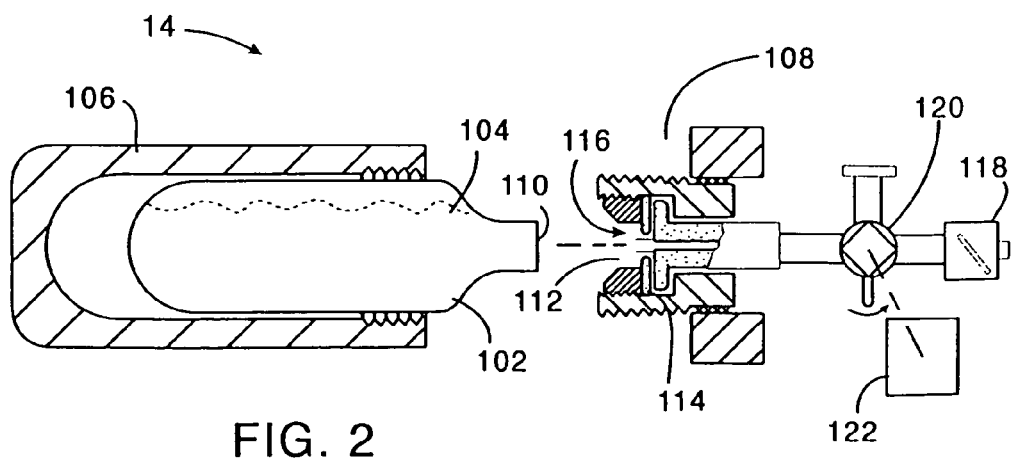
FIG. 2 is an exploded cross-sectional view of a cryogenic fluid supply system for use in the cryosurgical system of FIG. 1.

Cryogenic fluid delivery system 14 is illustrated in FIG. 2. Delivery system 14 makes use of a disposable cartridge 102 containing a cryogenic fluid 104. Cartridge 102 is received in a casing 106, and the casing threadably engages a fitting 108. By placing cartridge 102 in casing 106 and threading fitting 108 to the casing, a frangible seal 110 of the cartridge can be breached by a protruding tube 112 of the fitting. Fitting 108 may include a sealing body such as a rubber washer 114 to avoid leakage of cooling fluid 104, while the fitting and casing 106 may include gripping surfaces to facilitate breaching seal 110.

Once seal 110 has been breached by fitting 108, cryogenic cooling fluid 104 passes through a lumen 116 through the fitting and on toward the balloon surface. Coupling of fluid delivery system 14 to cooling/angioplasty balloon catheter 12 is facilitated by including a detachable connector 118 along the cooling fluid flow path, the connector typically comprising a luer fitting which sealingly engages fluid supply port 42 of the catheter. While connector 118 is here shown closely coupled to fitting 108, it should be understood that the fluid flow path may follow a longer, and optionally flexible path. In fact, aspects of the present invention will find uses with standard reusable cryogenic fluid supply system.

In fluid delivery system 14 illustrated in FIG. 2, a simple stopcock 120 is disposed between fitting 108 and connector 118. Stopcock 120 allows the cryogenic system operator to pierce seal 110 of cartridge 102 while setting up the system, and to later manually initiate flow of the cooling fluid by turning a lever of the stopcock. A port on stopcock 120 may be in fluid communication with the open cooling fluid path to verify cooling fluid pressure, temperature, or the like. Alternatively, the stopcock port may be isolated from the cooling fluid path when the stopcock opens.

Casing 106 and fitting 108 may comprise a variety of polymer and/or metallic materials. In the exemplary embodiment, casing 106 and at least a portion of fitting 108 are off-the-shelf items sized and adapted to receive and open a standard, commercially available pressurized fluid cartridge. The casing and seal opening components of the fitting may be fabricated by assembling and/or modifying components sold commercially by iSi Gmbh located in Vienna, Austria.

Cartridge 102 may be transported, stored, and optionally, used at room temperature. The cryogenic cooling fluid sealed within cartridge 102 may comprise $CO_2$, $N_2O$, AZ-50™ fluorocarbon, and/or a variety of alternative cryogenic cooling fluids. As these fluids are at quite high pressures within cartridge 102, they may be in the form of a liquid or gas/liquid mixture, even at room temperature. The pressure of cooling fluid 104 within cartridge 102 will often be greater than 400 psi, preferably being about 500 psi or more at room temperature. It should be understood that the cartridge pressure will decreased during the treatment as cooling fluid is consumed. Advantageously, the quantity of cooling fluid 104 may be such that the cryosurgical system (including cryogenic fluid supply 14 and catheter 12) cool and maintain a target tissue within a predetermined temperature range for a time within a predetermined time range by the time the cooling fluid is consumed from the canister. In other words, by selecting the proper fluid supply cartridge and catheter structures, the cryogenic therapy may be self-terminating without active intervention by an electronic control system, the operator, or the like. Cooling flow may cease when the fluid pressure within cartridge 102 is equal to ambient pressure, or may optionally be interrupted when the pressure drops below some threshold value.

Canister 102 will typically comprise a metallic structure. Suitable cartridges will hold quantities of cryogenic cooling fluid that are sufficient to cool the target tissue to the treatment temperature range for a time in the predetermined time range. Cartridges might have volumes between 2 cc and 100 cc (depending in part on the flash expansion temperatures of the cryogenic fluid), and may contain between about 5 g and 30 g of cooling fluid. A typical cartridge might contain a quantity of $N_2O$ in a range from about 5 ml to about 20 ml, ideally having about a 10 ml or 8 grams of $N_2O$ liquid at about 750 psi. Conveniently, such cartridges are commercially available for use in whipped cream dispensers. As explained below, canister 102 may be at room temperature or even chilled, but will preferably be warmed gently prior to use.

Although the above discussion occasionally refers to structures and techniques for enhancing the efficiency of cryogenic cooling, known cryogenic cooling techniques are capable of inducing temperatures well below the preferred treatment temperature ranges for use with the present invention. To moderate the cooling of the target tissue and provide antiproliferative benefits, the systems of the present invention may optionally rely on thermal insulation 72, as described above with reference to FIG. 1. Alternatively, a motor 122 may drivingly engage stopcock 120 so as to intermittently interrupt the flow of cooling fluid to the balloon. By cycling of the cooling fluid flow on and off, the present invention takes advantage of the thermal transients of the cooling system to prevent the tissue from reaching the low temperatures associated with a steady state cooling flow.

A variety of structures might be used to intermittently interrupt the flow of cooling fluid to the cryosurgical probe. In the embodiment of FIG. 2, an output shaft of an electrical motor assembly might be attached to a modified commercially available medical stopcock valve. Suitable motors might be powered from a standard wall outlet or batteries, and a reduction drive unit might be used to reduce the speed of the stopcock valve rotation to about one cycle per second. The drive motor may have a fixed speed to provide a temperature within a single predetermined temperature range, or may have a variable speed to actively control the temperature by varying the cycle speed, to alter the predetermined treatment temperature range for a particular treatment, and/or to provide the predetermined temperature range given a particular ambient condition, cryosurgical probe configuration, and the like.

Figure 3A:
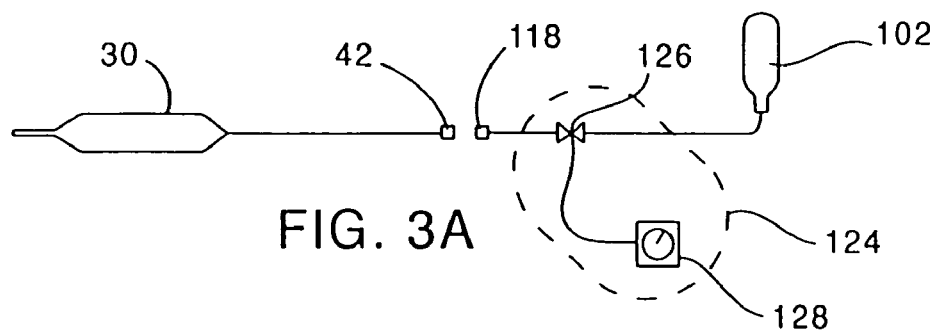
FIGS. 3A–3C schematically illustrate alternative flow interrupters for moderating the treatment temperatures of a cryosurgical system.
Figure 3B:
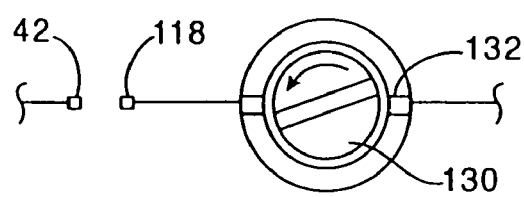
Figure 3C:
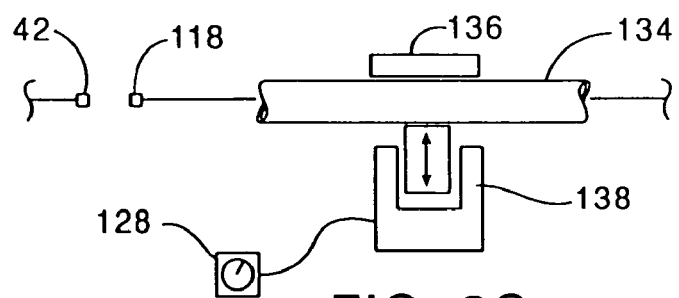
Figure 4:
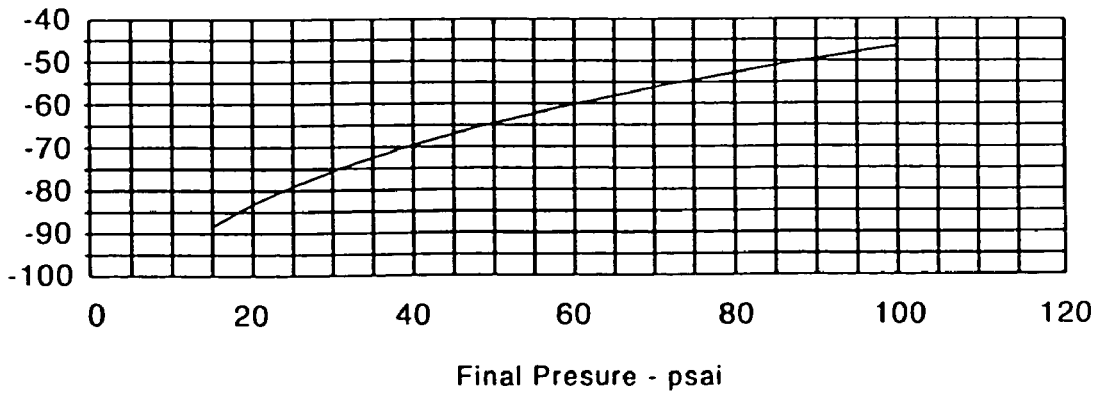
FIG. 4 illustrates cryogenic cooling temperatures provided by expansion of $N_2O$.

Referring now to FIGS. 3A through C, alternative cooling fluid interrupters 124 may comprise a solenoid valve 126 coupled to a timer 128. Solenoid valve 126 will preferably have a relatively low (dead) space, and will generally have a non-metallic body. Timer 128 may comprise an electromechanical timer, a circuit (such as an R-C timing circuit), or the like. Fabricating the solenoid valve body of a non-metallic material can help avoid the conduction of energy out of the system. Minimizing dead space in the flow path of the valve helps the valve from acting as an expansion chamber, which might otherwise rob energy from the system.

Referring now to FIG. 3B, a motor-driven rotating valve provides fluid communication from cartridge 102 to balloon 30 when a passage of the valve member 130 is aligned with a passage of the valve body 132, and blocks flow when the passage of the valve member is blocked by the valve body. This is the general case of the motor driven stopcock illustrated in FIG. 2. A variety of valve passage configurations might be used to provide multiple flow cycles per rotation of valve member 130. For example, the valve member may include a pair of orthogonal passages in an "X" configuration, thereby providing four flow cycles per rotation of the valve member. Flow can further be modified by changing the diameter of the passage or passages within valve member 130, the configuration of passages in valve body 132, the speed of rotation of the valve, and the like. Advantageously, a variety of flow cycles can be achieved.

Referring now to FIG. 3C, cooling fluid flow may alternatively be pulsed by intermittently impinging on a deformable cooling flow conduit 134. Suitable conduits might include a polyamide tube having an inner diameter in a range from about 0.012" to about 0.035" with a relatively thick tubal wall. An exemplary deformable conduit comprises a polyamide tube having an inner diameter of 0.016" and a relatively thick wall of about 0.0015", and also having a PTFE lining of about 0.0005".

Deformable conduit 134 may be pinched between a flat plate 136 and solenoid 138. Suitable small solenoids may be battery powered, and may optionally include a mechanical advantage mechanism to provide enough force to substantially or entirely occlude the cooling flow. Alternatively, a pressurized cylinder/piston arrangement might be used, thereby providing significantly higher forces for a given size. Such a pneumatic cylinder may be powered by any source of pressurized fluid, including an external pressurized air source, cartridge 102, or the like. Regardless of the specific pinch actuator, cycling of the flow cycle may again be provided by a timer 128, which may comprise an electromechanical timer, an R-C circuit, a mechanical or pressure actuated timing mechanism, or the like. It should be understood that the timer may be incorporated into the pinch actuation mechanism.

The benefits from the use of a flow interrupter can be understood with reference to FIGS. 4 and 5A through C. If cartridge 102 contains $N_2O$ at 750 psi, and if the cartridge is placed in an ice bath (thereby providing a convenient and reproducible initial condition), flash expansion of the cooling fluid to a pressure between atmospheric (14.7 psi) and 100 psi will result in cryogenic fluid temperatures in a range from about −45° C. to about −90° C. Such low temperatures are useful, for example, for therapies in which cryogenic ablation of tissues is desired. Surprisingly, it may be beneficial to gently warm the cartridge to enhance the fluid pressure and cooling system performance. Hence, alternative predetermined initial conditions might be provided by warming canister 102, preferably to about body temperature (with a hot plate, water bath, or the like) or even by holding the canister in a person's pocket (which may warm the canister to about 33° C.). Still further predetermined initial temperatures may simply comprise operating room temperature.

To provide apoptosis and/or programmed cell death so as to inhibit hyperplasia and/or neoplasia of a blood vessel related to angioplasty, stenting, rotational or directional atherectomy, or the like, it will often be desirable to provide more moderate cryogenic treatment temperatures. A wide variety of other therapies may also benefit from these treatment temperatures, including the formation of cryogenic lesions within the coronary atrium for treatment of atrial fibrillation, and the like. As a particular example, the cardiac tissue ablation devices and methods described in PCT Patent Application WO 98/49957, published on Nov. 12, 1998 (the full disclosure of which is incorporated herein by reference) might benefit from treatment temperatures significantly higher than about −30° C., in other words, significantly warmer than cooled tissue temperatures provided by many cryosurgical methods.

Figure 5A:
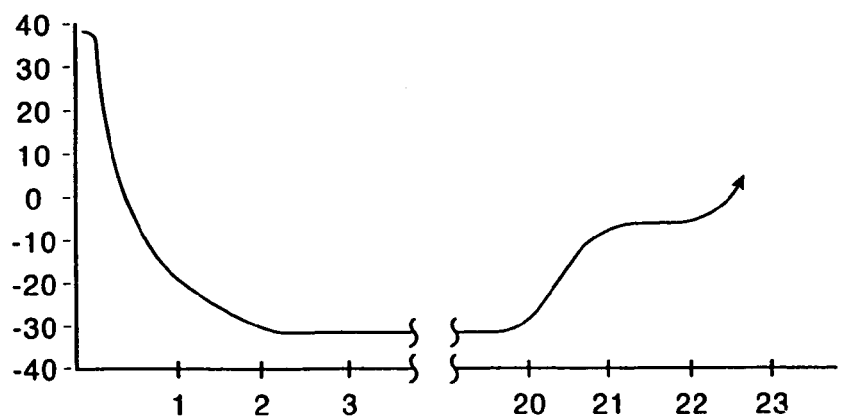
FIGS. 5A–5C graphically illustrate theoretical and measured treatment temperatures provided by an endovascular cryogenic balloon catheter system including the cryogenic fluid supply of the present invention.

Referring now to FIG. 5A, manually opening stopcock 120 of cryogenic fluid supply system 14 illustrated in FIG. 2 will typically result in a steady state flow of cooling fluid to balloon 30, resulting in a tissue temperature profile which quickly (often in about 2 seconds or less) drops down to a temperature of about −30° C. or less. Engaged blood vessel region will remain at this low temperature until cooling fluid 104 is fully consumed. Such cold treatment temperatures may induce necrosis, or may possibly be moderated by providing an insulation material between the cooling fluid and the engaged tissue, by narrowing the exhaust gas port so as to raise the pressure within balloon 30, or the like. The limited quantity of cooling fluid in cartridge 102 limits the treatment time without requiring active intervention by the surgeon.

Figure 5B:
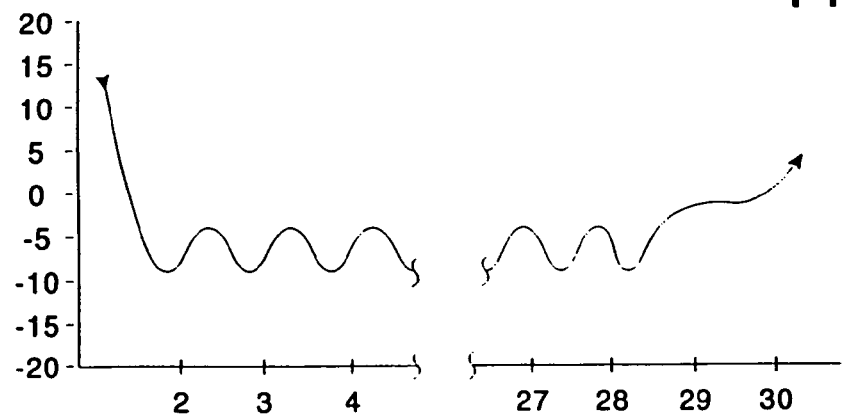

Referring now to FIG. 5B, cryogenic treatment temperatures can be modulated by intermittently cycling fluid flow. Specifically, flow is reduced and/or stopped significantly before the tissue reaches the nadir temperature. At this point, the body will absorb energy out of the system, raising the temperature of the treatment tissue. The interrupter may cycle the flow on and off to keep the system at a relatively stable temperature for the duration of treatment. Ideally, the on and off cycling can be controlled by a simple fixed timer so as to reach a temperature between about −5° C. and about −25° C. during each cycle. In the exemplary embodiment, the tissue is maintained within a temperature range from about −5° C. to about −25° C. throughout at least some of, and often most of, the thermal cycles. In some embodiments, a temperature feedback mechanism may be employed to modify the cooling cycles by altering a drive signal provided from controller 18 to the interrupter.

Figure 5C:
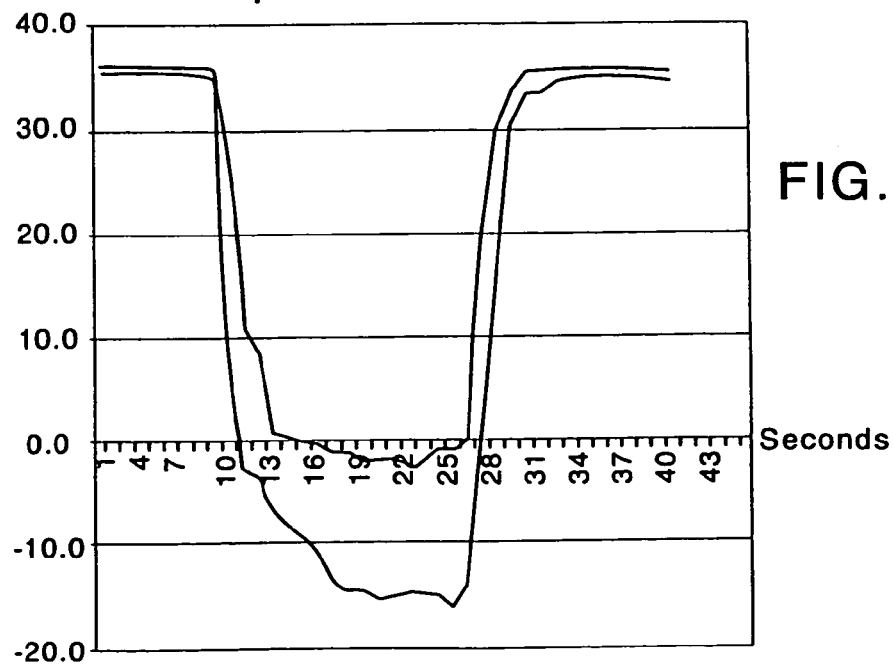

Referring now to FIG. 5C, a cryogenic cooling balloon having a diameter of about 2.5 mm and a length of about 4 cm was cooled by a $N_2O$ cartridge having a volume of about 10 cc. The cartridge was at about body temperature when flow began, providing a pressure of about 750 psi. A stopcock disposed along the flow path between cartridge 102 and balloon 30 was rotated at a speed of about one rotation per second by an electric motor. Balloon 30 was placed in body temperature water in this benchtop experiment, and temperatures were measured at an outer surface of the balloon. These experiments produced the treatment temperatures shown in these two different experimental cooling runs.

Figure 6A:
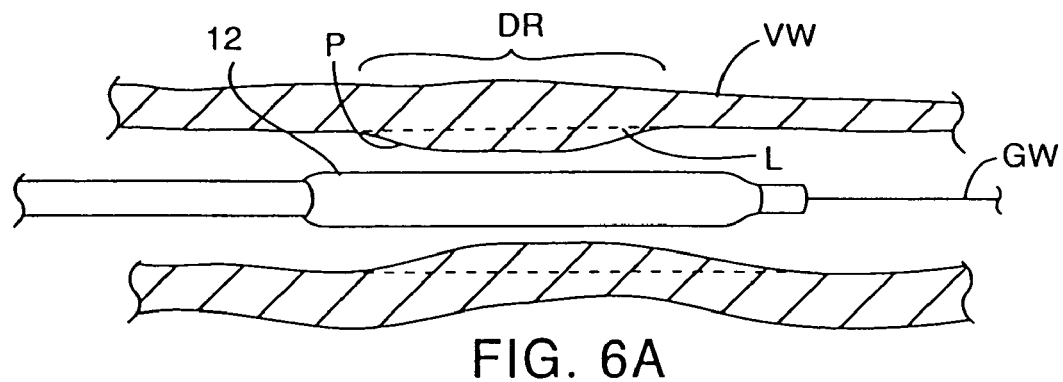
FIGS. 6A–6C are partial cross-sections schematically illustrating the method of the present invention for inhibition of hyperplasia.
Figure 6B:
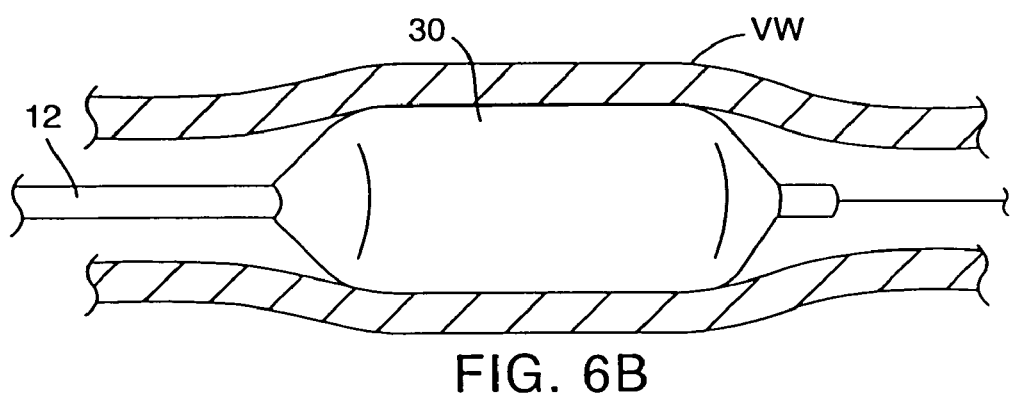
Figure 6C:
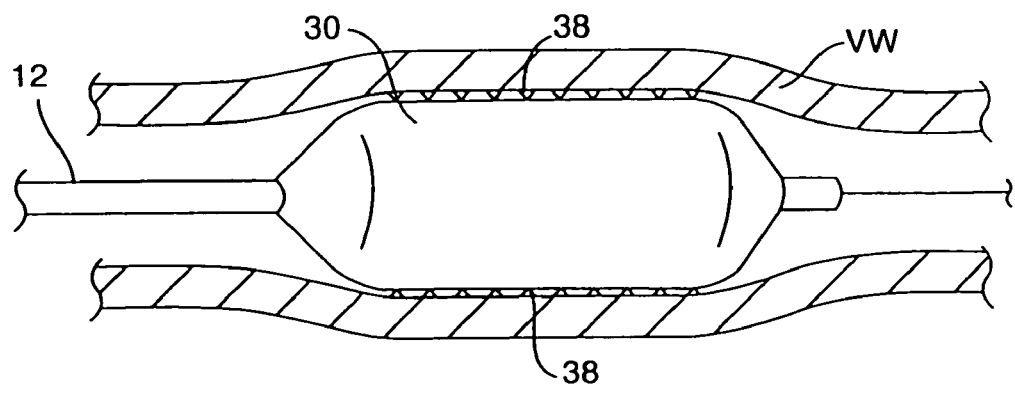

A method for using the modulated temperature cryogenic system 10 is illustrated in FIGS. 6A–6C. Typically, catheter 12 is introduced into the vasculature through an introducer sheath, most often using the widely known Seldinger technique. A guidewire GW is maneuvered through the vessel, and catheter 12 is advanced over the guidewire and positioned adjacent diseased portion DP a vessel wall VW.

Once balloon 30 is in position, the balloon can be inflated in a conventional manner to dilate the vessel, as illustrated in FIG. 6B. As can be understood with reference to FIG. 10, dilation may occur using an outer angioplasty balloon using conventional contrast fluid 40 to facilitate fluoroscopically directing a dilation procedure. Alternatively, the vessel may be dilated using a separate angioplasty catheter, an axially displaced angioplasty balloon, or using the cryogenic balloon itself. In still further alternatives, cryogenic cooling may be initiated prior to or during dilation. Regardless, cooling will preferably be effected by coupling a disposable cartridge to balloon 30 so that a cryogenic cooling fluid contained within the cartridge is transmitted to the balloon. Cooling flow between the cartridge and balloon 30 will be interrupted intermittently so as to modulate the treatment temperature, so that a surface layer 88 of vessel wall VW thermally engaged by balloon 30 cycles within a treatment temperature range from about −5° C. to about −25° C. for a time in a range from about 10 to about 60 seconds. As a result, this treated tissue layer undergoes apoptosis, thereby avoiding and/or reducing the proliferative response of the luminal wall to dilation.

As can also be understood with reference to FIGS. 6A–6C, plaque P or other occlusive matter may coat a portion of the vessel's lumen L. To treat the vessel wall tissues lining lumen L at the desired treatment temperature, balloon 30 may be cooled so that an outer surface of the balloon has a temperature significantly below the desired tissue treatment temperature range. Specifically, balloon 30 may be cooled to have an outer surface temperature selected to compensate for a thickness of occlusive matter disposed between the balloon surface and the target vessel tissue, with the selected balloon temperature typically decreasing with increasing occlusive matter thickness. The thickness of the occlusive matter may be measured in a blood vessel using a variety of techniques, including intravascular ultrasound (IVUS), fluoroscopy, and the like.

While the exemplary embodiments have been described in some detail, by way of example and for clarity of understanding, a variety of modifications, changes, and adaptations will be obvious to those of skill in the art. For example, a variety of endovascular therapies may benefit from the antiproliferative effects of the present invention, including angioplasty, stenting, directional and rotational atherectomy, and the like. Alternative treatment probes may also benefit from the moderated cryogenic treatment temperatures provided by the interrupted cooling fluid flow described hereinabove, including open surgical procedures effected by manipulating a hand-held rigid cryosurgical probe shaft supplied from conveniently cryosurgical fluid supply systems. Where ablation of a tissue most easily accessed through the vasculature is desired, the use of a disposable cartridge in combination with a flexible endovascular catheter may allow lesions having a predetermined size to be formed, with the total amount of cooling limited by the amount of cryogenic cooling fluid available within the cartridge. Hence, the scope of the present invention is limited solely by the appended claims.

What is claimed is:

1. A method for treating a diseased region of a blood vessel to a desired tissue treatment temperature range, the diseased region of the blood vessel having occlusive material between a vessel lumen and a vessel wall, the method comprising:
   measuring a thickness of the occlusive material between the vessel lumen and the vessel wall;
   positioning a balloon catheter within the vessel lumen adjacent the occlusive material;
   selecting an outer surface temperature to compensate for the thickness of the occlusive material, the outer surface temperature being lower than the target tissue temperature range;
   introducing a cooling fluid into the balloon catheter such that the cooling fluid vaporizes and cools an inner balloon catheter surface, an outer balloon catheter surface being disposed over the inner balloon catheter surface;
   controlling vaporization within the balloon so as to cool the outer surface of the balloon catheter below the target tissue temperature range according to the selected outer surface temperature such that the temperature of the vessel wall is within the target temperature range.

2. The method of claim 1, further comprising inhibiting heat transfer between the inner balloon surface and the outer balloon surface.

3. The method of claim 2, wherein the heat transfer inhibiting step comprises disposing an insulation material between the cooling fluid and the outer balloon catheter surface.

4. The method of claim 1, wherein the occlusive material measuring step is performed using intravascular ultrasound (IVUS).

5. The method of claim 1, wherein the desired tissue treatment temperature range is between about −5° C. and −25° C.

6. The method of claim 1, wherein the selecting step decreases outer surface temperatures with increasing occlusive material thicknesses.

7. The method of claim 1, wherein the vaporization controlling step comprises cycling a cooling fluid supply valve according to a regular period on/off cycle.

* * * * *